United States Patent [19]

Cohen

[11] 4,433,440
[45] Feb. 28, 1984

[54] PROSTHESIS FORMED BY INNER AND OUTER INFLATABLE CONTAINERS

[76] Inventor: I. Kelman Cohen, 5104 Cary St. Rd., Richmond, Va. 23226

[21] Appl. No.: 15,436

[22] Filed: Feb. 26, 1979

[51] Int. Cl.³ .......................... A61F 1/24; A41C 3/10
[52] U.S. Cl. ......................................................... 3/36
[58] Field of Search .......................... 3/36; 273/65 C; 152/340, 429, 339, 341

[56] References Cited

U.S. PATENT DOCUMENTS

| | | | |
|---|---|---|---|
| 2,780,266 | 2/1957 | McLeod | 152/340 |
| 2,964,084 | 12/1960 | Tubbs | 152/341 |
| 3,663,968 | 5/1972 | Mohl et al. | 3/36 |
| 3,852,832 | 12/1974 | McGhan et al. | 3/36 |
| 3,852,833 | 12/1974 | Koneke et al. | 3/36 |
| 3,919,724 | 11/1975 | Sanders et al. | 3/36 |
| 3,934,274 | 1/1976 | Hartley, Jr. | 3/36 |

OTHER PUBLICATIONS

Hartley, Jr., "Specific Applications of the Double Lumen Prosthesis", *Clinics in Plastic Surgery*, pp. 247-263, vol. 3, No. 2, 4/76.

*Primary Examiner*—Clifford D. Crowder
*Attorney, Agent, or Firm*—Cushman, Darby & Cushman

[57] ABSTRACT

A breast prosthesis comprising inner and outer flexible containers, each having a self-sealing valve associated therewith. The valves are arranged in such a fashion that each container can be separately filled with fluid. The prosthesis is implanted in a deflated state and each container is filled in turn before closing the incision.

6 Claims, 6 Drawing Figures

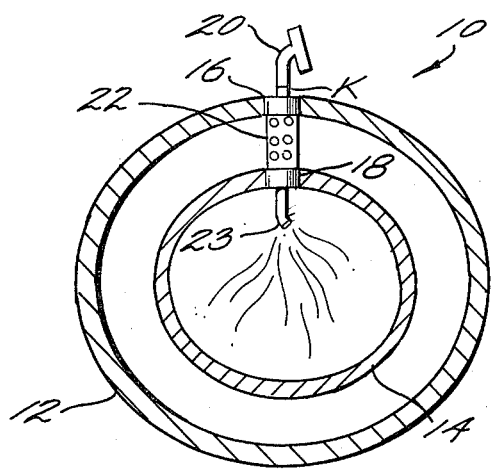
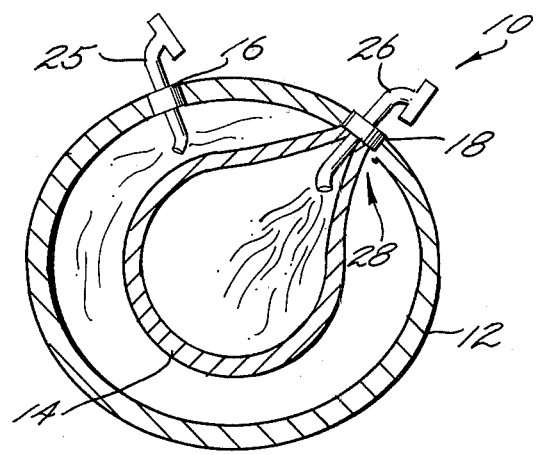
Fig. 1  Fig. 2
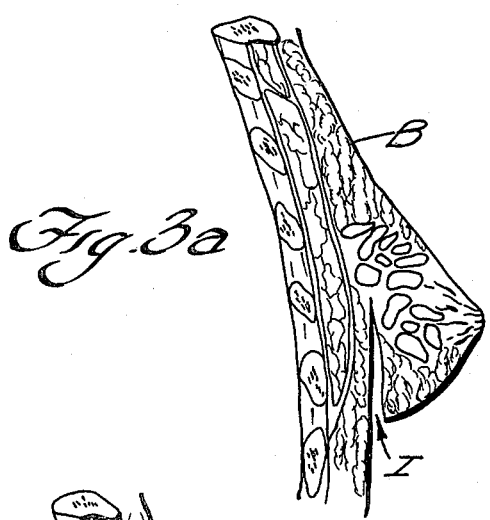
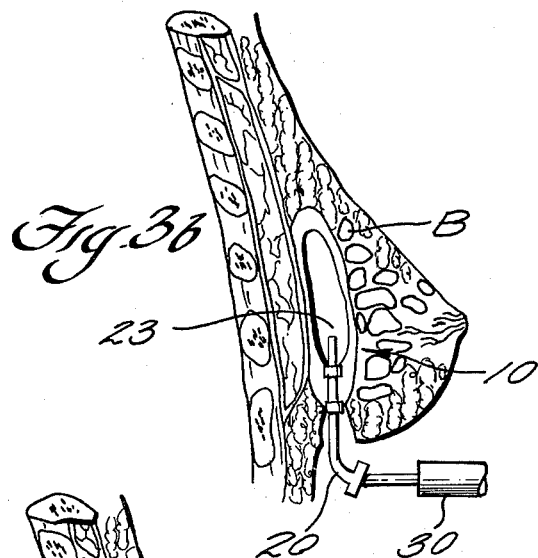
Fig. 3a  Fig. 3b
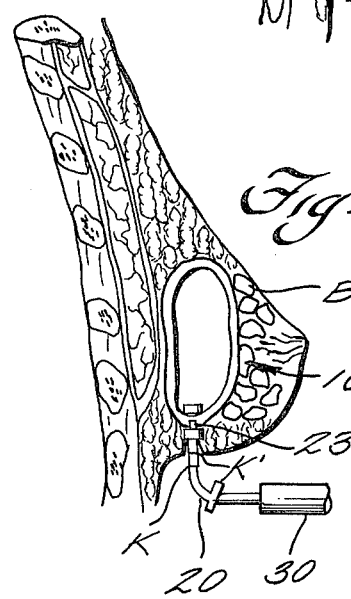
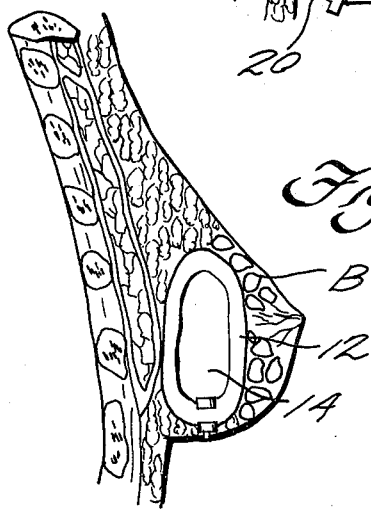
Fig. 3c  Fig. 3d

PROSTHESIS FORMED BY INNER AND OUTER INFLATABLE CONTAINERS

BACKGROUND AND SUMMARY OF THE INVENTION

Prosthetic devices for practicing augmentation mamoplasty conventionally are of two types: implants made of a silicone elastomer shell filled with a polymerized silicone gel, or silicone breast implants made of a silicone elastomer shell containing a valve which is filled with saline or other physiologic solutions. Neither type of device has been entirely successful, both experiencing early or late fluid or gel leakage through the shell, the leakage being more common in the fluid-filled implants but more dangerous for the gel-filled implants. With leakage from the gel-filled implant there is a chance for morbidity with gel extravasation in human tissue, and some silicon gel polymers are small enough to bleed through the elastomer shell. For these reasons, and also because various drugs (such as corticosteriods) can be added to the fluid-filled implants which might improve breast softness, and breast prenchyma can be studied easier by mammograms if implants are fluid-filled rather than gel-filled, fluid-filled implants are desirable.

Previous attempts have been made to solve some of the problems of conventional gel-filled implants by the creation of a two-chamber implant including an inner chamber containing silicone gel and an outer chamber which is filled with physiologic fluid via a self-sealing valve in the operating room. Such attempts have been described in an article entitled "Specific Applications of the Double Lumen Prosthesis" by John H. Hartlye, Jr., M.D., "Clinics and Plastic Surgery" Vol. 3, No. 2, pages 247–263 (April, 1976). The outer chamber is the fluid-filled chamber, and it can be deflated by percutaneous needle puncture if the breast becomes too firm as a result of capsule contracture. While such an approach can be successful, the problem of mammographic obliteration is still present.

According to the present invention a breast prosthesis, and a method of practicing augmentation mamoplasty utilizing the breast prosthesis, are provided which overcome many of the drawbacks associated with prior art prosthesis and techniques. An unfilled implant according to the present invention may be inserted more easily and through a smaller incision than conventional prefilled (or partially prefilled) implants. The breasts prosthesis according to the present invention comprises an outer inflatable container of flexible biological implant material (e.g. a silicone elastomer shell); an inner inflatable container of flexible biological implant material, substantially concentric with the outer container; and a self-sealing or operator sealed valve associated with each container and for admitting fluid to the container with which it is associated, and for sealing the fluid within the container after filling thereof. When self-sealing valves are used, they can be of any conventional type such as shown in U.S. Pat. Nos. 3,853,832 or 3,919,724, or such as those manufactured by Heyer-Schulte, Inc. The prosthesis also preferably comprises removable fluid-filling means for penetrating the self-sealing valves and providing the introduction of fluid therethrough.

Two different embodiments of the prosthesis may be provided. In one embodiment, the removable fluid-filling means comprises a single tubular member penetrating both self-sealing valves at the same time, with mounting means being provided for mounting the tubular member for movement from a position penetrating both self-sealing valves to a position penetrating only the self-sealing valve of the outer container, to a position penetrating neither valve. A mounting means preferably comprises a perforated tubular member having a diameter slightly larger than the diameter of the tubular member extending between the self-sealing valves and operatively connected thereto.

In the second embodiment, the removable fluid filling means comprises a pair of tubular members, one associated with each of the self-sealing valves, for penetrating a respective self-sealing valve, each of the tubular members extending to the exterior of the outer container. The inner container is connected to the outer container at one of the self-sealing valves which valve is common to the inner and outer containers.

In both embodiments, the inner and outer containers are preferably filled with physiologic fluid, such as saline or saline including corticosteriods.

The method of augmentation mamoplasty according to the present invention includes forming an incision in the breast area, and placing the prosthesis, preferably with both containers deflated, through the incision beneath the breast. Then one of the containers (preferably the inner container) is filled with a physiologic fluid and the self-sealing valve associated with that container is allowed to seal the fluid within the container. Then the other container (the outer container) is filled with the physiologic fluid, allowing the self-sealing valve associated with that container to seal the fluid within that container, and then the incision is closed.

It is the primary object of the present invention to provide an advantageous breast prosthesis and a method utilizing the same in augmentation mamoplasty. This and other objects of the invention will become clear from an inspection of the detailed description of the invention, and from the appended claims.

BRIEF DESCRIPTION OF THE DRAWINGS

FIG. 1 is a side view partly in cross-section and partly in elevation of one embodiment of an exemplary prosthesis according to the present invention;

FIG. 2 is a side view partly in cross-section and partly in elevation of another embodiment of a breast prosthesis according to the present invention; and FIGS. 3a through 3d are step by step schematic showings of an exemplary method of practicing augmentation mamoplasty utilizing a prosthesis like that of FIG. 1.

DETAILED DESCRIPTION OF THE DRAWINGS

An exemplary prosthesis according to the present invention is shown generally at 10 in the drawings. The prosthesis 10 includes an outer inflatable container 12 of flexible biological implant material, such as a silicone elastomer shell, and an inner inflatable container 14 substantially concentric with the outer container 12. Self-sealing valves 16 and 18 are associated with the outer and inner containers 12, 14 respectively, the valves 16, 18 for admitting fluid to the container with which it is associated and for sealing the fluid within the container after filling thereof. The self-sealing valves 16, 18 may be of any conventional type such as shown in U.S. Pat. No. 3,852,832 and 3,919,724, or those commercially available from Heyer-Schulte, Inc. Operator sealed valves may be utilized if desired, except that valve 18 in the FIG. 1 embodiment should be self-sealing.

Both containers 12, 14 are adapted to be filled with a physiologic fluid, such as saline or saline including corticosteriods. A removable fluid filling means is provided for penetrating the valves 16, 18 and to provide the introduction of fluid therethrough. In the embodiment of the invention illustrated in FIG. 1, the fluid-filling means comprises a single tubular member 20 penetrating both valves at the same time, with a perforated tubular member 22 extending between and operatively connected to the valves 16, 18. The perforated tubular member 22 comprises means for mounting the tubular member 20 for movement from a position penetrating both valves 16, 18 to a position penetrating only valve 16, to a position penetrating neither valve. The perforated tubular member 22 has a diameter slightly larger than the diameter of tubular member 20, and provides for ready guiding of the member 20 through and out from engagement with the valves 16, 18. The perforations in the tube 22 allow fluid to be introduced into the space between the outer 12 and inner 14 containers when the end 23 of tubular member 20 is disposed in the volume defined by the perforated tubular member 22.

Indicia preferably are provided on the member 22 to indicate the position of the open end 23 thereof with respect to the containers 12, 14. When indicia K (see FIG. 1) is seen, it is known that the member 22 penetrates the inner container 14, and when indicia K' (see FIG. 3c) is seen, it is known that the opening 23 is between the exterior walls of the containers 12, 14.

In the embodiment of the prosthesis 10 illustrated in FIG. 2, the removable fluid-filling means comprises a pair of tubular members 25, 26, one associated with each of the valves 16, 18 respectively. In this embodiment the inner container 14 is operatively connected at 28 to the outer container 12, with the valve 18 providing a common interconnection at point 28.

A method of practicing augmentation mamoplasty utilizing a prosthesis 10 generally as illustrated in FIG. 1 will now be described with respect to FIGS. 3a through 3d. The prosthesis utilized in FIGS. 3a through 3d is the same as that illustrated in FIG. 1 only the perforated tubular member 22 has been eliminated.

FIG. 3a shown a non-augmented breast B, and the first step in the practice of the method of the invention is the formation of an incision I in the breast area. Then, as illustrated in FIG. 3b, the prosthesis 10 is placed through the incision beneath the breast B, and the fluid-filling tubular member 20 thereof is connected up to a source 30 of physiologic fluid. The source of physiological fluid can comprise a syringe filled with a predetermined desired volume of physiological fluid (depending upon the enlargement to be accomplished), such as shown in co-pending application 751,215 filed Dec. 16, 1976, and now U.S. Pat. No. 4,143,428, the disclosure of which is hereby incorporated by reference herein.

Once the prosthesis 10 is in place as illustrated in FIG. 3b, with indicia K showing, a predetermined quantity of physiologic fluid is introduced into the inner container 14 through the tubular member 20, and then the tubular member 20 is withdrawn so that the free end 23 thereof no longer passes through the valve 18, but is disposed between the containers 12 and 14, as illustrated in FIG. 3c, with indicia K showing. In this position, the inner container 14 is filled and sealed while the outer container 12 is still deflated. Then, a further predetermined quantity of physiologic fluid is introduced through the tubular member 20 into the outer container 12, and then the tubular member 20 is withdrawn from the valve 16, the valve 16 sealing the fluid within the container 12. Then the incision I is closed, and the now augmentated breast B will have the configuration illustrated in FIG. 3d.

The prosthesis and method of practicing augmentation mamoplasty utilizing the same, according to the present invention, have a number of advantages associated therewith. Since only physiologic fluid is used there is no potential for danger from silicone gel leakage. Additionally, pharmacologic agents can be added to improve breast softness if efficacious, and antibiotics may be added. Since the implants 10 are preferably deflated originally, they can be placed through a smaller incision I than a prefilled gel containing implant. Radiographic studies of the breast will be more accurate since no gel-filled implants are utilized. Finally, the leakage problem normally associated with conventional saline-filled prosthesis is minimized since leakage of the outer container 12 will not result in significant diminution in breast size which would necessitate re-operation.

While the invention has been described above particularly with respect to augmentation mamoplasty, it is readily apparent that it is equally applicable to reconstruction techniques after subcutaneous masectomy or breast reconstruction after breast cancer ablation.

It will thus be seen that according to the present invention an advantageous breast prosthesis and method of utilizing same have been provided. While the invention has been herein shown and described in what is presently conceived to be the most practical and preferred embodiments thereof, it will be apparent to those of ordinary skill in the art that many modifications may be made thereof within the scope of the invention, which scope is to be accorded the broadest interpretation of the appended claims so as to encompass all equivalent structures and methods.

What is claimed is:

1. A breast prosthesis comprising
an outer inflatable container of flexible biological implant material;
an inner inflatable container of flexible biological implant material, substantially concentric with said outer container;
a valve associated with each container and for admitting fluid to the container with which it is associated, and for sealing the fluid within the container after filling thereof;
removable fluid-filling means for penetrating said valves and providing the introduction of fluid therethrough; and
wherein both valves are self-sealing and wherein said removable fluid-filling means comprises a single tubular member penetrating both self-sealing valves at the same time, and means mounting said tubular member for movement from a position penetrating both self-sealing valves to a position penetrating only the self-sealing valve of said outer container, to a position penetrating neither valve.

2. A prosthesis as recited in claim 1 wherein both valves are self-sealing, and wherein said means mounting said tubular member for movement includes a perforated tubular member having a diameter slightly larger than the diameter of said tubular member and extending between said self-sealing valves and operatively connected thereto.

3. A prosthesis as recited in claim 1 further comprising indicia formed on the exterior of said tubular member for indicating the penetration of said tubular member with respect to said containers.

4. A prosthesis as recited in claim 3 wherein both said inner and outer containers are filled with physiologic fluid.

5. A method of practicing augmentation mamoplasty utilizing a breast prosthesis including inner and outer substantially concentric inflatable containers of flexible biological implant material, each having a valve associated therewith, and wherein a removable tubular fluid-filling member extends from exteriorly of both the containers through the valves and the valves are self-sealing; said method comprising the steps of substantially sequentially (a) forming an incision in the breast area;

(b) placing the prosthesis, with both containers deflated, through the incision beneath the breast;

(c) filling the at least one deflated container with a physiologic fluid, and providing sealing of the valve associated with that container to seal the fluid within the container; by:

(d) filling the inner container with a physiologic fluid by introducing fluid through the tubular member into the inner container, and then withdrawing the tubular member from passage through the self-sealing valve of the inner container while it remains passing through the self-sealing valve of the outer container, to seal the fluid within the inner container, and (e) filling the outer container with a physiologic fluid by introducing fluid through the tubular member into the outer container, and then withdrawing the tubular member from passage through the self-sealing valve of the outer container, and to seal the fluid within the outer container; and (f) closing the incision.

6. A method as recited in claim 5 wherein the physiologic fluid introduced into the containers is selected from the group consisting essentially of saline and saline containing corticosteriods or other physiological materials.

* * * * *